United States Patent
Rosenfeld et al.

(10) Patent No.: US 7,803,145 B2
(45) Date of Patent: Sep. 28, 2010

(54) DRAPEABLE ABSORBENT ARTICLE

(75) Inventors: Leonard G. Rosenfeld, Yardley, PA (US); Hien V. Nguyen, East Windsor, NJ (US)

(73) Assignee: McNeil-PPC, Inc., Skillman, NJ (US)

( * ) Notice: Subject to any disclaimer, the term of this patent is extended or adjusted under 35 U.S.C. 154(b) by 442 days.

(21) Appl. No.: 11/589,655

(22) Filed: Oct. 30, 2006

(65) Prior Publication Data

US 2007/0219519 A1 Sep. 20, 2007

Related U.S. Application Data

(60) Provisional application No. 60/782,796, filed on Mar. 16, 2006.

(51) Int. Cl.
*A61F 13/15* (2006.01)
(52) U.S. Cl. ............ 604/385.01; 604/367; 604/374; 604/375; 604/378
(58) Field of Classification Search ............ 604/367, 604/366, 378, 385.101, 385.16, 385.22, 384, 604/374, 375, 377, 400, 385.23, 385.01; 442/224, 246, 414
See application file for complete search history.

(56) References Cited

U.S. PATENT DOCUMENTS

| | | | |
|---|---|---|---|
| 6,497,691 B1 | 12/2002 | Bevins | |
| 6,503,234 B1 | 1/2003 | Canuel | |
| 2003/0114822 A1* | 6/2003 | Collando et al. | 604/385.01 |
| 2004/0236297 A1 | 11/2004 | Drzewiecki | |
| 2005/0004547 A1 | 1/2005 | Lavash | |
| 2005/0106965 A1* | 5/2005 | Wevers et al. | 442/85 |
| 2005/0131371 A1 | 6/2005 | Fell | |

FOREIGN PATENT DOCUMENTS

| | | |
|---|---|---|
| EP | 705583 A1 | 4/1996 |
| EP | 1029522 A2 | 8/2000 |
| EP | 1637109 A2 | 3/2006 |
| WO | 199822061 A1 | 5/1998 |

* cited by examiner

*Primary Examiner*—Jacqueline F. Stephens

(57) ABSTRACT

An absorbent article including a cover layer, a barrier layer and an absorbent system arranged between the cover layer and the barrier layer, the absorbent article being drapeable and possessing the absorbency attributes required of a sanitary napkin.

20 Claims, 4 Drawing Sheets

DRAPEABLE ABSORBENT ARTICLE

CROSS-REFERENCE TO RELATED APPLICATIONS

This application claims priority of U.S. Provisional Patent Application No. 60/782,796, filed on Mar. 16, 2006.

FIELD OF THE INVENTION

The present invention generally relates to sanitary absorbent articles and in particular to feminine sanitary absorbent napkins that are thin, highly absorbent, and drapeable.

BACKGROUND OF THE INVENTION

Externally worn, sanitary absorbent napkins are one of many kinds of feminine protection devices currently available. The development of materials having a high liquid absorption capacity per unit volume has allowed the required overall thickness of sanitary napkins to be reduced, thereby providing a product which is more comfortable and less obtrusive to wear. Thin, flexible, sanitary napkins of this type are disclosed, for example, in U.S. Pat. No. 4,950,264 (hereinafter "the '264 patent") to T. W. Osborne III.

The term "flexible" as used in the prior art is generally used to describe an article's resistance to deformation when an external load is applied thereto. For example, the '264 patent purports to disclose a sanitary napkin having a "low flexural resistance" when an external load is applied to the sanitary napkin by means of a plunger mechanism.

However a "flexible" definition of the type provided in the '264 patent does not measure the overall "drapeable" characteristics of an absorbent article. That is, an article may have a "low flexural resistance" and yet not be "drapeable" as defined herein. The term "drapeable" or "drapeability" as used herein means the tendency of an article to hang in a vertical fashion due to gravity when held in a cantilevered manner from one end of said article. Drapeable articles also tend to conform to the shape of an abutting surface, for example a drapeable sanitary napkin will tend to conform to the body during use, thereby enhancing comfort.

Textile fabrics, and other cloth-like materials, which are used in clothing, tend to posses this "drapeable" characteristic. Clothing made from textile fabrics possessing this "drapeable" characteristic tend to conform to, and move with, the wearer, resulting in enhanced comfort to the user.

An absorbent article possessing these "drapeable" characteristics may increase comfort to the wearer. That is, an article that is sufficiently "drapeable" such that it conforms to the space defined between the user's thighs and the user's undergarment, may provide enhanced comfort to the wearer. In contrast, if an absorbent article is not sufficiently drapeable the wearer may experience discomfort and be conscious of the absorbent article. Additionally, if such article bunches or deforms, there is a tendency for the article to maintain its resulting shape, thereby providing inadequate protection.

Thus, although the prior art may disclose "flexible" absorbent articles, there is still a need for absorbent articles, and in particular sanitary napkins, that are drapeable and also possess the absorbency attributes required of such absorbent articles.

SUMMARY OF THE INVENTION

In view of the foregoing, the present invention provides according to a first aspect of the invention an absorbent article including a cover layer, a barrier layer, an absorbent system arranged between the cover layer and the barrier layer, the absorbent system including superabsorbent polymer (SAP), and wherein the absorbent article has a drape angle at x=50 of less than 80° and a drape angle at x=100 of less than 50°.

BRIEF DESCRIPTION OF THE DRAWINGS

Examples of embodiments of the present invention will now be described with reference to the drawings, in which.

DETAILED DESCRIPTION OF THE INVENTION

Preferred embodiments of the present invention comprise absorbent articles, and in particular sanitary napkins, that are thin, flexible, drapeable and possess absorbency attributes required of sanitary napkins. Test methods are provided below for evaluating the absorbency and drapeable attributes of articles according to the present invention.

Test Procedures

To test an absorbent article according to the test methods set forth herein a minimum of twelve product samples are required.

Vertical Hang Test

In order for an absorbent article to behave in a garment like manner, the absorbent article must be sufficiently drapeable to hang in a substantially vertical manner when held from one end of the article in a cantilevered fashion. The Vertical Hang Test measures the tendency of an absorbent article to hang in this manner.

Figures 5, 6:
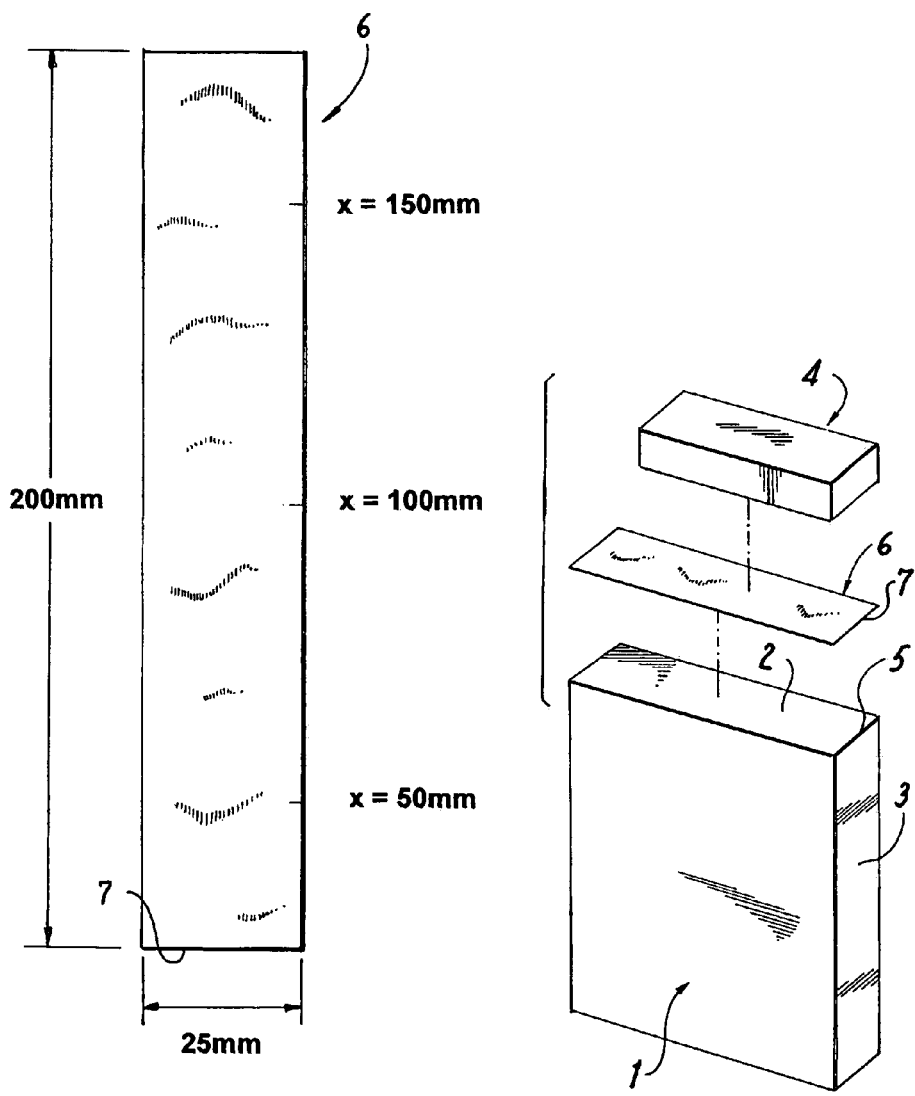
FIG. 5 is a schematic view of a test strip used in the Vertical Hang Test described herein.
FIG. 6 and FIG. 7 are schematic drawings illustrating the manner in which the Vertical Hang Test is conducted.
Figure 7:
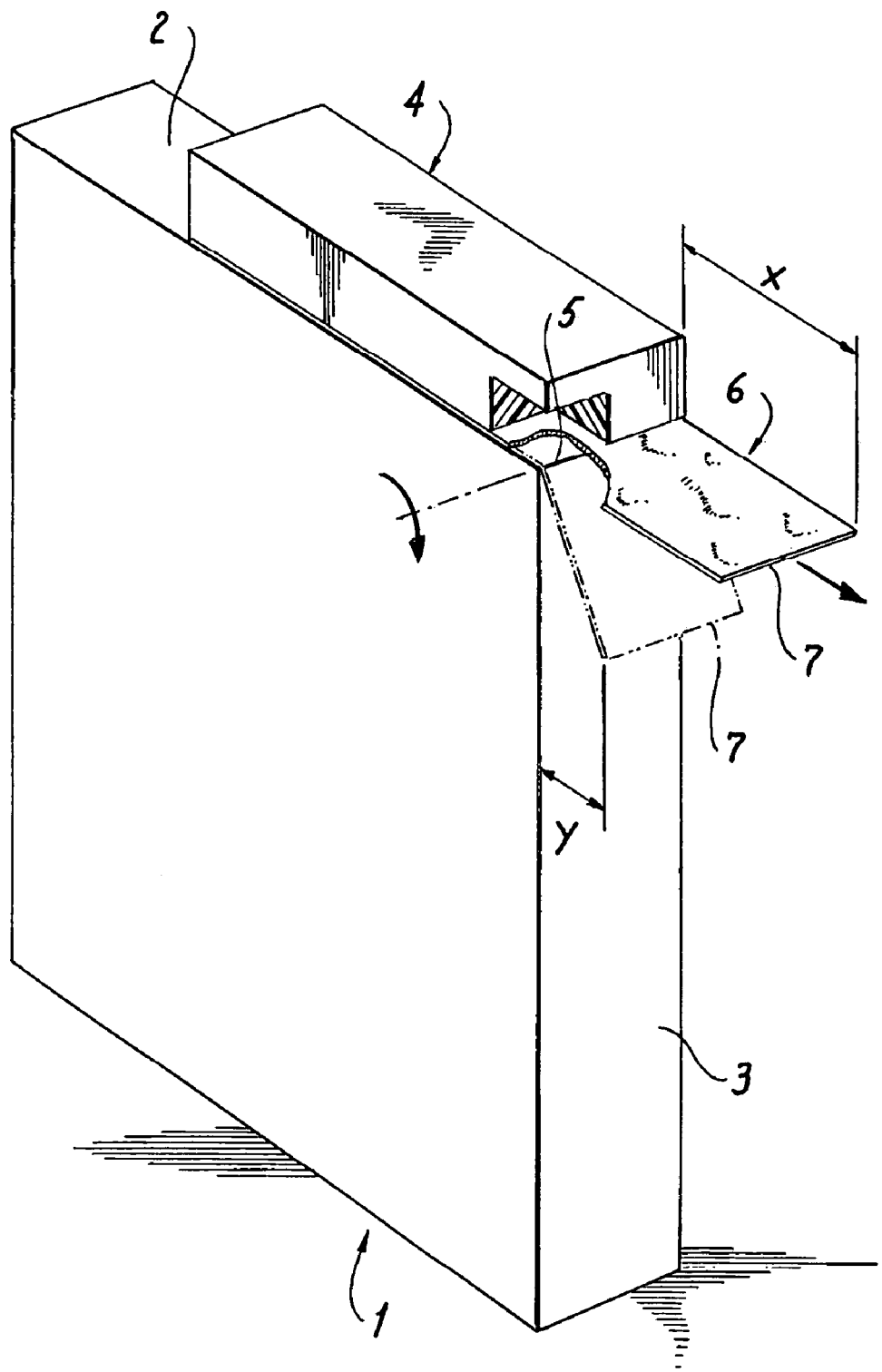

Reference will be made to FIGS. 5-7 in describing the Vertical Hang Test. In order to conduct the Vertical Hang Test three (3) identically constructed absorbent articles are required.

A 200 mm by 25 mm test strip, identified by the reference numeral 6 in FIG. 5, is cut from the absorbent portion of the absorbent article to be tested. The test strip 6 should be cut along the longitudinal centerline 34 of the absorbent article such that the center of the test strip 6 is located at the area of the article intended to be arranged over the vaginal opening during use. In addition, the test strip 6 is cut such that the 200 mm portion thereof extends along the longitudinal centerline 34 of the article. In the event that the absorbent article from which the test strip is to be taken has an overall length less than 200 mm, then the largest test strip possible should be cut from the article along the longitudinal centerline 34 thereof.

If the absorbent product has residual fold lines, which are common in products that are trifolded, the product is flattened by hand as much as possible prior to cutting the test strip 6 from the article. Any release paper or other materials intended to be removed prior to using the article should also be removed prior to cutting the test strip. Any exposed adhesive surface should be covered with baby powder or similar material prior to cutting the test strip.

After a test strip 6 is cut from each of the three product samples, each test strip 6 is marked with a felt tip pen or the like at locations x=50 mm, x=100 mm and x=150 as measured from one transverse edge 7 of the test strip, as shown in FIG. 5. After each test strip 6 has been cut and marked as described above each strip 6 is tested as described below with reference to FIGS. 6 and 7.

For clarity, when dimensions are described in connection with the test procedure, depth is the direction into the page in FIGS. 6 and 7 and L, W and D will be used to refer to length, width, and depth respectively.

In order to carry out the test method a rectangular box 1, shown in FIGS. 6 and 7, is constructed from lexan having dimensions of 200 mm (L)×200 mm (W)×25 mm (D). The corners of the box 1 are square. The box 1 includes a first surface 2 and a orthogonally arranged second surface 3. The location where the first surface 2 intersects with the second surface 3 will be referred to herein as the lip 5. Surface 2 measures 25 mm (D)×200 mm (L). Surface 3 measures 25 mm (D)×200 mm (W).

The test strip 6 is placed on horizontal surface 2 so that the transverse edge 7 of the test strip is aligned with the lip 5. A flat lexan plate 4 is placed over the test strip 6 such that the end of the plate is coplanar with surface 3 of the box. The lexan plate 4 has dimensions of 50 mm (L)×5 mm (W)×25 mm (D).

The lexan plate 4 is then partially lifted so that the test strip 6 can be pulled out until the marked x=50 mm line on the test strip is aligned with the lip 5 of the box and the lexan plate 4 is then placed back down. In this manner, a 50 mm section of the test strip 6 is permitted to hang beyond the lip 5 and the lexan plate 4 functions to hold the test strip 6 in place. After this process the test strip 6 will be in the state shown in phantom in FIG. 7, i.e. the test strip 6 will hang in a vertically depending fashion.

After the test strip 6 is arranged so that a 50 mm section thereof extends beyond the lip 5, the distance "y" from the transverse edge 7 of the strip 6 to the outer face of surface 3 is measured.

From the known value "x" and the measured value "y" the drape angle can be calculated as follows:

Drape Angle=sin$^{-1}$(y/x)

The drape angle indicates the tendency of an article to drape in a vertical fashion. For an article that does not drape at all, i.e. an article that extends out from surface 1 in a purely horizontal manner, the drape angle will be 90°. For an article that is completely drapeable, i.e. the article hangs such that it extends vertically down surface 3, the calculated drape angle will be 0°.

Based on the above formulae the drape angle for x=50 is calculated and recorded. The test strip 6 is then arranged such that a 100 mm section thereof extends beyond the lip 5, i.e. x=100. The new "y" value is measured and the drape angle for x=100 is calculated and recorded. The test strip 6 is then arranged such that a 150 mm section thereof extends beyond the lip 5, i.e. x=150. The new "y" value is measured and the drape angle for x=150 is calculated and recorded.

The above described test procedure is repeated for each of the two remaining test strips. The calculated drape angle for x=50 for each of the three test strips is averaged, the calculated drape angle for x=100 for each of the three test strips is averaged, and the calculated drape angle for x=150 for each of the three test strips is averaged. In this manner an average drape angle for x=50, x=100 and x=150 is obtained.

The above described test method was conducted on the following products:
Inventive Sample 1 (described in detail below);
Stayfree Freestyle Sanitary Napkin (New Zealand);
Stayfree Ultrathin Regular (United States).

The average drape angle at x=50, x=100 and x=150 for each of the products is provided in the table below.

|  | Drape Angle x = 50 mm | Drape Angle x = 100 mm | Drape Angle x = 150 mm |
| --- | --- | --- | --- |
| Stayfree Freestyle | 85° | 69° | 26° |
| Stayfree Ultrathin Regular | 90° | 82° | 55° |
| Inventive Sample 1 | 58° | 25° | 11° |

As shown above, absorbent articles according to the present invention preferably have a drape angle at x=50 of less than 80°, more preferably less than 70°, and most preferably less than 60°.

As shown above, absorbent articles according to the present invention preferably have a drape angle at x=100 of less than 50°, more preferably less than 40°, and most preferably less than 30°.

As shown above, absorbent articles according to the present invention preferably have a drape angle at x=150 of less than 25°, more preferably less than 20° and most preferably less than 15°.

Procedure for Determining Absorbency Index (AI)

In order for an absorbent article to function properly it must have good absorbent properties to give the user confident protection against soiling of garments and leakage. The "Absorbency Index" (AI) (as defined herein) of an absorbent article is a measure of the article's fluid handling properties. The Absorbency Index (AI) of an absorbent article is determined from a composite of two fluid handling properties, Rewet (R) and Fluid Penetration Time (FPT). The Absorbency Index (AI) as used herein is defined as follows:

$$\text{Absorbency Index} = AI = \left(\frac{6.27 - R}{6.12}\right) + \left(\frac{499 - FPT}{495}\right); \text{ where}$$

R=Rewet Value (grams)
FPT=Fluid Penetration Time (seconds)

The methods for determining the Rewet Value (R) and the Fluid Penetration Time (FPT) for an absorbent article are provided below. Nine new product samples, having the same construction as the products tested in the Vertical Hang Test described above, are required to conduct the Rewet Value (R) and Fluid Penetration Time (FPT) tests described below.

Three of the product samples are tested for Rewet Value (R) and Fluid Penetration Time (FPT) at a location on the article corresponding to the location on the article where the x=50 mm drape angle was measured in the Vertical Hang Test described above. AI at the x=50 mm location is calculated for each of the three tested products and averaged to obtain an average AI at the x=50 mm location.

Three of the product samples are tested for Rewet Value (R) and Fluid Penetration Time (FPT) at a location on the article corresponding to the location on the article where the x=100 mm drape angle was measured in the Vertical Hang Test described above. AI at the x=100 mm location is calculated for each of the three tested products and averaged to obtain an average AI at the x=100 mm location.

The final three product samples are tested for Rewet Value (R) and Fluid Penetration Time (FPT) at a location on the article corresponding to the location on the article where the x=150 mm drape angle was measured in the Vertical Hang Test described above. AI at the x=150 mm location is calculated for each of the three tested products and averaged to obtain an average AI at the x=150 mm location.

After testing the articles in the above manner an average AI at x=50 mm is obtained, an average AI at x=100 mm is obtained, and an average AI at x=150 mm is obtained. The highest average AI value and the lowest average AI are thrown out and the middle average AI value is considered to be the AI value for the article.

Absorbent articles according to the present invention preferably have an Absorbency Index (AI) of greater than about 1.5, more preferably greater than about 1.7 and most preferably greater than about 1.8. Inventive sample #1 described in detail below was determined to have an Absorbency Index of 1.84.

The fluid penetration time (FPT) and the rewet (R) test methods are described in further detail below.

Procedure for Measuring Fluid Penetration Time

Three product samples are used for the Fluid Penetration Time (FPT) procedure, for a given location (e.g. x=50).

Fluid Penetration Time is measured by placing a sample to be tested under a Fluid Penetration Test orifice plate. The orifice plate consists of a 7.6 cm×25.4 cm plate of 1.3 cm thick polycarbonate with an elliptical orifice in its center. The elliptical orifice measures 3.8 cm along its major axis and 1.9 cm along its minor axis. The orifice plate is arranged on the product sample to be tested at the selected location on the absorbent article to be tested (either x=50 mm, x=100 mm, x=150 mm). The longitudinal axis of the elliptical orifice is arranged parallel to the longitudinal axis of the product to be tested.

Test fluid was made of the following mixture to simulate bodily fluids: 49.5% of 0.9% sodium chloride solution (VWR catalog #VW 3257-7), 49.05% Glycerin (Emery 917), 1% Phenoxyethanol (Clariant Corporation Phenoxetol™) and 0.45% Sodium Chloride (Baker sodium chloride crystal #9624-05).

A graduated 10 cc syringe containing 7 ml of test fluid is held over the orifice plate such that the exit of the syringe is approximately 3 inches above the orifice. The syringe is held horizontally, parallel to the surface of the test plate. The fluid is then expelled from the syringe at a rate that allows the fluid to flow in a stream vertical to the test plate into the orifice and a stop watch is started when the fluid first touches the sample to be tested. The stop watch is stopped when a portion of the surface of the sample first becomes visible above the remaining fluid within the orifice. The elapsed time on the stop watch is the Fluid Penetration Time in seconds. This fluid penetration time (FPT) may then be used in the Absobency Index (AI) equation set forth above.

Procedure for Measuring Rewet Potential

The three product samples used for the Fluid Penetration Time (FPT) procedure, for a given location (e.g. x=50), are also used for the Rewet Potential test described below.

The rewet potential is a measure of the ability of a napkin or other article to hold liquid within its structure when the napkin contains a relatively large quantity of liquid and is subjected to external mechanical pressure. The rewet potential is determined and defined by the following procedure.

The apparatus for the Rewet Potential test is the same as that set forth above with regard to the FPT test and further includes a quantity of 3 inch×4 inch rectangles of Whatman #1 filter paper from Whatman, Inc. Clifton, N.J. and a weighing machine or balance capable of weighing to an accuracy of ±0.001 g, a quantity of said Whatman paper, a standard weight of 2.22 kg (4.8 pounds) having dimensions 5.1 cm (2 inches) by 10.2 cm (4.0 inches) by approximately 5.4 cm (2.13 inches) which applies a pressure of 4.14 kPa (0.6 psi) over the 5.1 by 10.2 cm (2 inches by 4 inches) surface.

For purposes of the test procedure set forth herein, the same three product samples used for the fluid penetration test should be used for the rewet potential test. After the test fluid is applied within the orifice plate in the FPT test described above, and as soon as the cover layer of the napkin first appears through the top surface of the fluid, the stop watch is started and an interval of 5 minutes is measured.

After 5 minutes have elapsed, the orifice plate is removed and the napkin is positioned on a hard level surface with the cover layer facing upwards.

A fifteen (15) layer stack of the pre-weighed filter paper is placed on and centered over the wetted area and the standard 2.22 kg weight is placed on top of the filter paper. The filter paper and the weight are arranged over the absorbent article such that they are centered over the area to which the fluid was applied. The filter paper and the weight are arranged such that their longer dimensions are aligned with the longitudinal direction of the product. Immediately after placing the paper and weight on the product, the stopwatch is started and after a 3 minute interval has elapsed the standard weight and filter paper are quickly removed. The wet weight of the filter paper is measured and recorded to the nearest 0.001 grams. The rewet value is then calculated as the difference in grams between the weight of the wet 15 layers of filter paper and the dry 15 layers of filter paper. This calculated rewet value (R) may then be used in the Absorbency Index (AI) equation set forth above.

Procedure for Measuring the Average Thickness of a Sanitary Article

The thickness measurement procedure described below should be conducted on three product samples prior to conducting the vertical hang test described above and after the product samples have been removed from any packaging, any release paper has been removed, and after the product has been powdered with talc or the like. The thickness measurement of the product should be taken at the location of the article intended to be placed over the vaginal opening during use The absorbent articles according to the present invention preferably have a thickness of less than 2.5 mm, more preferably less than 2.0 mm, and most preferably less than about 1.5 mm. The procedure for measuring the thickness of an absorbent article is described below.

The apparatus required to measure the thickness of the sanitary napkin is a footed dial (thickness) gauge with stand, available from Ames, with a 2" diameter foot at a pressure of 0.07 psig and a readout accurate to 0.001". A digital type apparatus is preferred. If the sanitary napkin sample is individually folded and wrapped, the sample is unwrapped and carefully flattened by hand. The release paper is removed from the product sample and it is repositioned back gently across the positioning adhesive lines so as not to compress the sample, ensuring that the release paper lies flat across the sample. Flaps (if any) are not considered when taking the thickness.

The foot of the gauge is raised and the product sample is placed on the anvil such that the foot of the gauge is approximately centered on the location of interest on the product sample. When lowering the foot, care must be taken to prevent the foot dropping onto the product sample or undue force being applied. A load of 0.07 p.s.i.g. is applied to the sample and the read out is allowed to stabilize for approximately 5 seconds. The thickness reading is then taken. This procedure is repeated for at least three product samples and the average thickness is then calculated.

Inventive sample #1 described in detail below was measured to have a thickness of 1.44 mm.

Description of Preferred Embodiments

Figure 1:
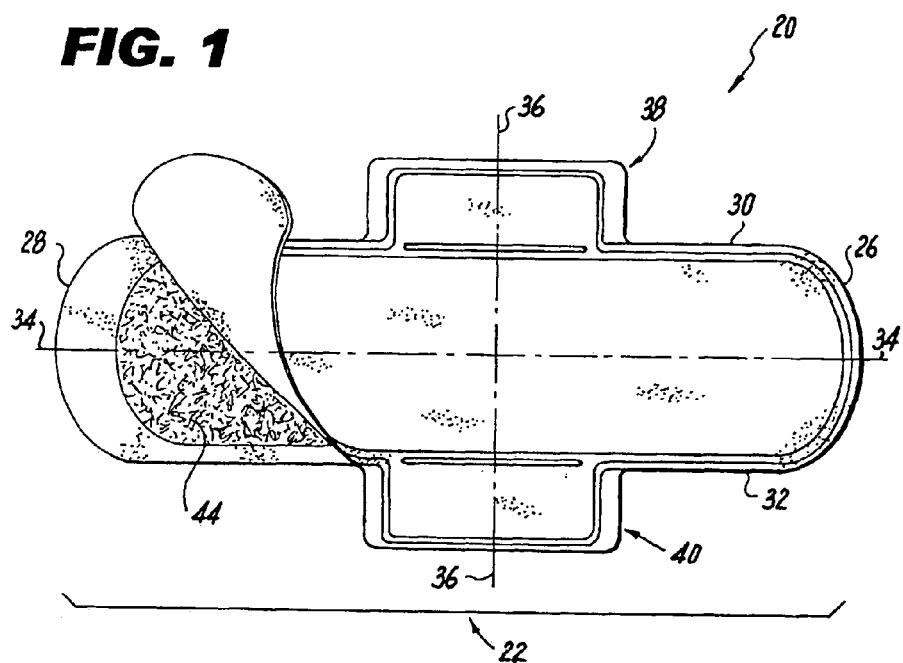
FIG. 1 is a top plan view of a sanitary napkin in accordance with an embodiment of the present invention, the cover layer of the sanitary napkin being partly removed to show the absorbent system.
Figure 2:
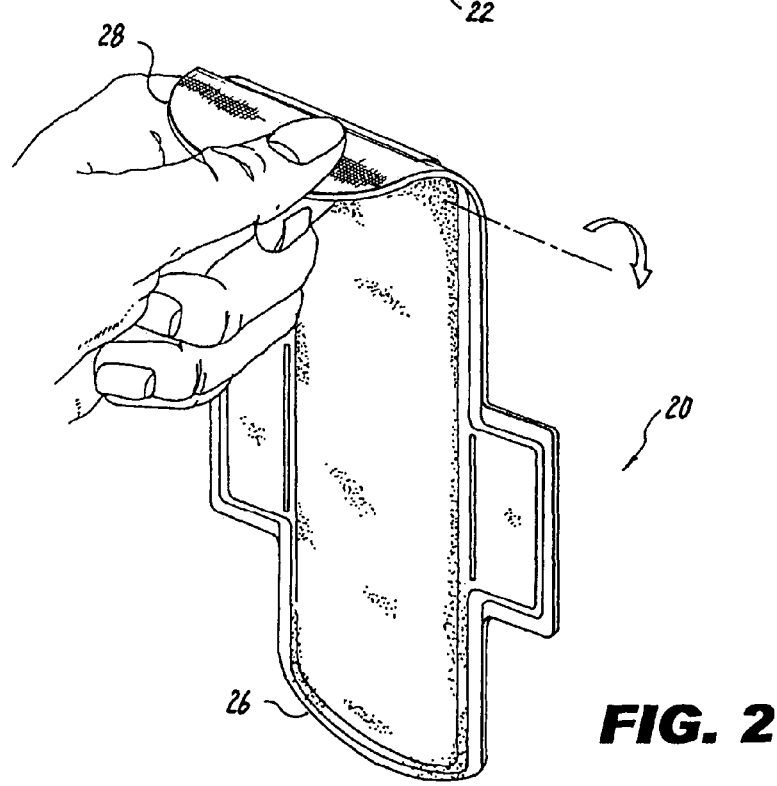
FIG. 2 is perspective view of the sanitary napkin shown in FIG. 1, depicted in a position attained when the sanitary napkin is held in a cantilevered manner from one end of the napkin.
Figure 3:
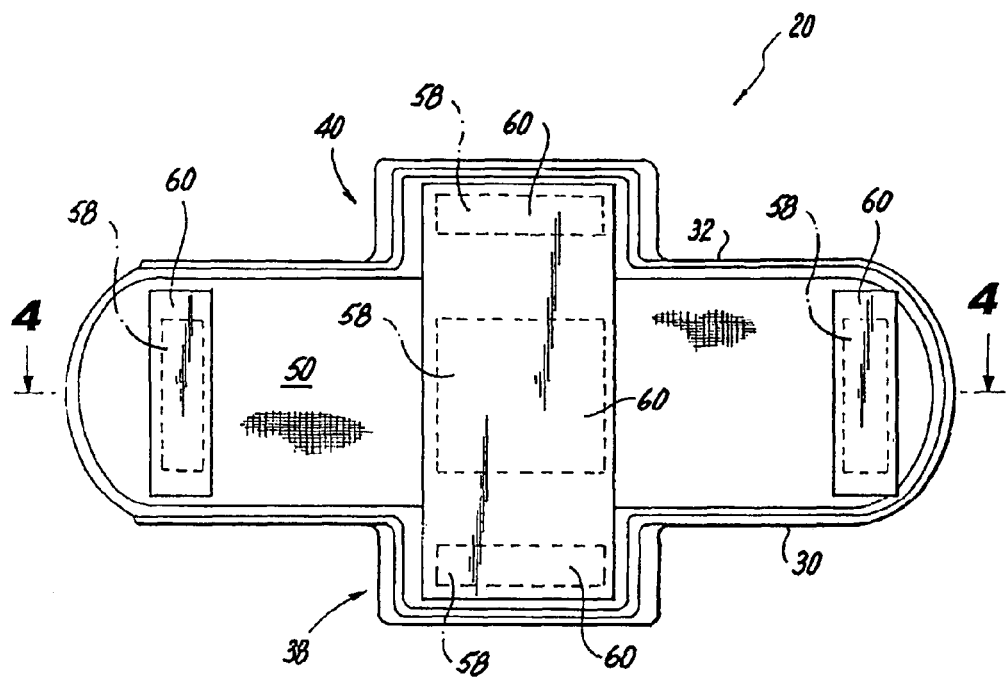
FIG. 3 is a bottom plan view of the sanitary napkin shown in FIG. 1.

Referring to FIGS. 1 and 2, there is shown an embodiment of the present invention, a feminine sanitary napkin 20.

The sanitary napkin 20 has a main body 22 with a first transverse side 26 defining a front portion thereof and a second transverse side 28 defining a rear portion thereof. The main body also has two longitudinal sides, namely a longitudinal side 30 and a longitudinal side 32. The sanitary napkin 20 preferably has a thickness not exceeding about 2.5 mm, preferably the thickness is less than 2.0 mm, more preferably less than 1.5 mm.

The sanitary napkin 20 has a longitudinal centerline 34 that is an imaginary line bisecting the sanitary napkin 20 in two identical halves. Projecting laterally outward from each of the longitudinal sides 30, 32 is a flap 38 and 40 respectively. The main body 22 also has an imaginary transverse centerline 36 perpendicular to the longitudinal centerline 34 and simultaneously bisecting the flaps 38, 40.

Figure 4:
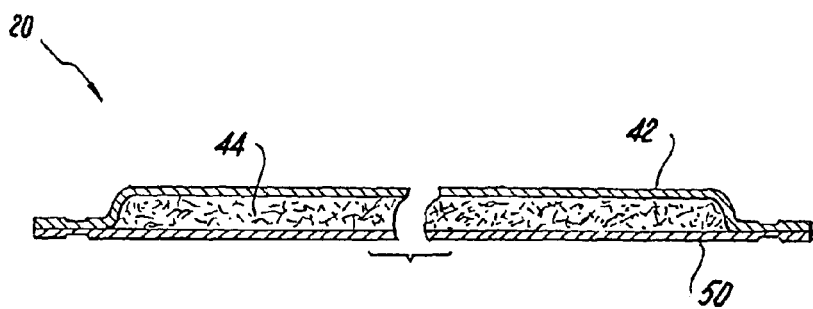
FIG. 4 is a cross sectional view taken along the longitudinal center line 4-4 of the sanitary napkin shown in FIG. 3.

As depicted in FIG. 4, the main body 22 is of a laminate construction and preferably comprises a fluid-permeable cover layer 42, an absorbent system 44 and a fluid-impervious barrier layer 50.

Main Body—Cover Layer

The cover layer 42 may be a relatively low density, bulky, high-loft non-woven web material. The cover layer 42 may be composed of only one type of fiber, such as polyester or polypropylene or it may include a mixture of more than one fiber. The cover may be composed of bi-component or conjugate fibers having a low melting point component and a high melting point component. The fibers may be selected from a variety of natural and synthetic materials such as nylon, polyester, rayon (in combination with other fibers), cotton, acrylic fiber and the like and combinations thereof. Preferably, the cover layer 42 has a basis weight in the range of about 10 gsm to about 75 gsm.

Bi-component fibers may be made up of a polyester layer and a an polyethylene sheath. The use of appropriate bi-component materials results in a fusible non-woven fabric. Examples of such fusible fabrics are described in U.S. Pat. No. 4,555,430 issued Nov. 26, 1985 to Chicopee. Using a fusible fabric increases the ease with which the cover layer may be mounted to the absorbent layer and/or to the barrier layer.

The cover layer 42 preferably has a relatively high degree of wettability, although the individual fibers comprising the cover may not be particularly hydrophilic. The cover material should also contain a great number of relatively large pores. This is because the cover layer 42 is intended to take-up body fluid rapidly and transport it away from the body and the point of deposition. Therefore, the cover layer contributes little to the time taken for the napkin to absorb a given quantity of liquid (penetration time).

Advantageously, the fibers which make up the cover layer 42 should not lose their physical properties when they are wetted, in other words they should not collapse or lose their resiliency when subjected to water or body fluid. The cover layer 42 may be treated to allow fluid to pass through it readily. The cover layer 42 also functions to transfer the fluid quickly to the other layers of the absorbent system 44. Thus, the cover layer 42 is advantageously wettable, hydrophilic and porous. When composed of synthetic hydrophobic fibers such as polyester or bi-component fibers, the cover layer 42 may be treated with a surfactant to impart the desired degree of wettability.

In one preferred embodiment of the present invention the cover is made from a spunlace nonwoven material having from about 0 to about 100% polyester and from about 0 to about 100% rayon. The spunlace material may also be made from about 10% to about 65% rayon and from about 35% to about 90% polyester. In lieu of, and/or in combination with the polyester, polyethylene, polypropylene or cellulosic fiber may be used with the rayon. Optionally, the material used for the cover layer may include binders such as thermoplastic binders and latex binders.

In another preferred embodiment of the present invention the cover is made from a spunlace nonwoven material and has a "fluid absorption time" (as defined below) of less than 100 s, preferably less than 50 s and most preferably less than 30 s.

In another preferred embodiment of the present invention the cover is made from a spunlace nonwoven material that is composed substantially entirely of "nonabsorbent fibers" and has a "fluid absorption time" (as defined below) of less than 100 s, preferably less than 50 s and most preferably less than 30 s.

The term "nonabsorbent fibers" as used herein means fibers that do not retain any fluid within the polymer matrix of the fiber body itself. Examples of suitable nonabsorbent fibers include polypropylene, polyester, polyethylene and bicomponent fibers made from combinations of polypropylene, polyester and polyethylene.

The surface of the nonabsorbent fibers may be rendered "permanently wetable" (hydrophilic) via suitable surface finishing compositions, such as appropriate surfactants as well as internal surfactants. The term "permanently wetable" as used herein means that the surface of the fibers retain their wetable characteristics after the spunlacing process. Specific examples of fibers whose surface is permanently wetable are commercially available and are set forth below in the examples.

Preferably spunlace materials according to the present invention include at least 20% of nonabsorbent fibers by weight that have a fiber surface that is permanently wetable, more preferably at least 35% nonabsorbent fibers by weight that have a fiber surface that is permanently wetable and most preferably at least 50% nonabsorbent fibers by weight that have a fiber surface that is permanently wetable.

"Composed substantially entirely of nonabsorbent fibers" as used herein means that preferably at least 90% of the fibers by weight in the spunlace cover material are nonabsorbent, more preferably at least 95% by weight are nonabsorbent, and most preferably 100% of the fibers by weight are nonabsorbent.

In another specific embodiment the cover material is a spunlace nonwoven material that contains between about 10% and 90% polypropylene fibers by weight and between 90% and 10% polyester fibers by weight, more preferably between about 35% and 65% polypropylene fibers by weight and 65% and 35% polyester fibers by weight, and the cover material has a fluid absorption time of less than 100 s, preferably less than 50 s and most preferably less than 30 s.

In those embodiments of the spunlace cover material according to the present invention wherein the spunlace cover includes a preformed web introduced prior to hydro entangling, the preformed web preferably makes up about 10% to about 50% by weight of the total cover weight. The preformed web material preferably has a basis weight in the range of about 5 gsm to about 20 gsm, and more preferably from about 10 gsm to about 15 gsm. The preformed is also preferably constructed from a nonabsorbent material such as polyethylene or polypropylene.

In the those embodiments of the present invention where the cover material is a spunlace material the cover preferably has a total basis weight of about 30 gsm to about 80 gsm and more preferably about 40 gsm to about 60 gsm.

Although preferred embodiments of the present invention employ fibrous nonwoven materials as the cover layer, apertured film materials may also be employed as the cover layer.

Procedure for Determining Fluid Absorption Time of Cover Material

As discussed above spunlace cover materials in accordance with the present invention preferably have a "fluid absorption time" (as defined below) of less than 100 s, preferably less than 50 s and most preferably less than 30 s.

The procedure for determining the fluid absorption time of a cover material is provided below.

First a test fluid was prepared, the test fluid having the following composition:

(a) 50 g of Acrysol G111 (commercially available from Rohm & Haas, Philadelphia, Pa.);
(b) 975 g of distilled water (72.8 dynes/cm); and
(c) 10 g of red dye (commercially available from Sigma-Aldrich Co., St. Louis, Mo.).

The resulting test fluid had a value of 42 dynes/cm.

The test procedure was conducted as follows:

(1) A 2" by 2" swatch of the cover material is laid flat on a level surface such as a table top. No absorbent material should be arranged under the cover material since this will effect the measured fluid absorption time;

(2) A 0.05 g drop of the test fluid is applied to the top surface of the material using an appropriate pipette. The terminal end of the pipette should be applied just above the top surface of the material so as to minimize the free fall of fluid but the terminal end of the pipette should not be positioned in direct abutment with the top surface of the material so as to force the test fluid into the material;

(3) After the drop of test fluid is applied to the material a stop watch is started and then the stop watch is stopped when the drop of fluid has fully entered into the material.

(4) The above described process is repeated for five material samples and the average fluid absorption time is calculated, this average being the "fluid absorption time" according to this method.

Examples of Spunlace Cover Materials

Three specific examples of cover materials according to the present invention are set forth below and two comparative examples are also provided. Each of the inventive spunlace covers were manufactured using conventional spunlacing techniques well known to those skilled in the art.

Spunlace Cover Example I a hydro entangled spunlace nonwoven web with a basis weight of 50 gsm comprised of 50% 2.0 dpf Type 130 HyEntangle WA (polypropylene) fibers available from Fibervisions Inc. Covington Ga. and 50% 1.4 dpf PET fibers Series 300 available from Sabic Inc., Sittard (The Netherlands). The 2.0 dpf Type 130 HyEntangle WA fibers are "permanently wetable" fibers.

Spunlace Cover Example II a hydro entangled spunlace nonwoven web with a total basis weight of 50 gsm comprised of a 10 gsm or 20% of total w/w % preformed web of spunbond PP introduced prior to hydro entangling available from PGI, Inc. Charleston SC code KO-CA-5 and 40 gsm or 80% of total w/w % of staple fibers that are 1.5 dpf PET fibers Type 203 available from Wellman Inc. Charlotte, N.C. In this example the permanently wettable "fibers" are introduced via the preformed spunbond PP web. In this embodiment the spunbond PP web is "permanently wettable".

Spunlace Cover Example III a hydro entangled spunlace nonwoven web with a basis weight of 50 gsm comprised of a 10 gsm or 20% 2.0 dpf Type 130 HyEntangle WA (polypropylene) fibers available from Fibervisions Inc. Covington Ga. and 40 gsm or 80% 1.5 dpf PET fibers Type 203 available from Wellman Inc., Charloette, N.C. The 2.0 dpf Type 130 HyEntangle WA fibers are "permanently wetable" fibers.

Comparative Spunlace Example I a hydroentangled spunlace nonwoven web with a basis weight of 50 gsm comprised of 100% 1.5 dpf PET fibers Type 203 available from Wellman Inc. Charlotte, N.C.

Comparative Spunlace Example II a hydro entangled spunlace nonwoven web available from Polymer Group Inc. Charleston, S.C. code JM-88-10-12 with a total basis weight of 50 gsm comprised of a 15 gsm or 30% of total w/w % spunbond PP introduced prior to hydro entangling available from PGI, Inc. Charleston S.C. and 35 gsm or 70% of total w/w % of staple fibers that are 1.5 dpf PET fibers Type 203 available from Wellman Inc. Charlotte, N.C.

The fluid absorption times for each of the above examples were determined and are provided in the chart below.

| Sample | Fluid Absorption Time, s N = 5 |
|---|---|
| Spunlace Example I | 25.7 |
| Spunlace Example II | 18.0 |
| Spunlace Example III | 58.6 |
| Comparative Spunlace Example I | >146.2 |
| Comparative Spunlace Example II | >200 |

The cover layer 42 may be embossed to the remainder of the absorbent system 44 in order to aid in promoting hydrophilicity by fusing the cover to the next layer. Such fusion may be effected locally, at a plurality of sites or over the entire contact surface of cover layer 42 and absorbent system 44.

Alternatively, the cover layer 42 may be attached to the absorbent system 44 by other means such as by adhesion.

Main Body—Absorbent System

In a specific example of the present invention the absorbent system 44 is composed primarily of SAP (superabsobent) powder deposited between the cover and barrier. Preferably the SAP is applied to an internal surface of either the cover layer, barrier layer, other to the surface of a layer arranged between the cover layer and the barrier layer. The SAP is preferably adhered to the internal surface of the cover, the internal surface of the barrier, or either surface of the layer arranged between the cover and barrier, using adhesive. For example, typical pressure sensitive adhesives such as Fuller 1491 available from the Fuller Corporation can be coated to the internal surface of the barrier to hold the SAP powder in place. SAP's with very rapid absorbency rates such as Sumitomo BA40B (Sumitomo Seika Chemical Companies Ltd., Osaka, Japan) have been found to be particularly well suited. For this construction, the SAP layer is preferably substantially uniform with a basis weight of at least 50 gsm and preferably between about 100 gsm and 150 gsm.

In one preferred embodiment of the invention the absorbent system consists of superabsorbent adhered to a tissue layer that is arranged between the cover and the barrier.

In another embodiment of the invention the absorbent layer may consist solely of superabsorbent adhered to either an internal surface of the cover or an internal surface of the barrier.

Preferred superabsorbents useful in the present invention have a very high "gel blocking ratio" (as defined in further detail below). The absorbency values and gel blocking values described below are based upon an absorption of 0.9% saline solution in a GAT (Gravimetric Absorbency Tester) device under a pressure of 0.01 psi. A detailed description of a GAT apparatus is described by McConnell in U.S. Pat. No. 4,357,827, the subject matter of which is hereby incorporated by reference. Suitable GAT testing systems are available from M/K Systems, Danners, Ma. A detailed description of the test method used to determine absorbency values of the SAP set forth above is provided below.

SAP was prepared for the test by first screening out the SAP using a 100-mesh screen (US Sieve Series) to isolate SAP that would remain on top of a 100-mesh screen.

The test cell of the GAT apparatus is adjusted such that is 1 cm above the level of the fluid reservoir. Whatman GF/A filter paper was placed on top of the test cell of the GAT apparatus, the test cell comprising a multi-hole plate. The filter paper functions insure that a continuous flow of test fluid is delivered to the SAP.

A test chamber was constructed from a 1-inch ID plexiglass tube having a first open end and a second end covered by a 100-mesh metal screen. An amount of 0.10 gram SAP powder was placed in the test chamber on top of the metal screen, this amount of SAP corresponding to 200 gsm. A 4.4 gram plexiglass puck machined to closely fit within, but not bind the cylinder, was placed on top of the powder to provide a nominal load of 0.01 psi.

The test chamber was placed on top of the filter paper so the outer surface of the screen is in abutment with the filter paper arranged on the GAT test cell. The test was run over 60 minutes, data on the amount of fluid absorbed was captured every 15 seconds by a computer. For the SAP sample, an absorbency curve was generated by plotting g/g capacity v. time.

A second test, as described above, was conduct on the same type of SAP used in the above test. However, in this second test an amount of 0.50 gram SAP powder was placed in the test chamber on top of the metal screen, this amount of SAP corresponding to 1000 gsm. The second test in all other respects were carried out as described above and a second absorbency curve was generated by plotting g/g capacity v. time.

A "gel blocking ratio" was determined from the ratio of the total capacity of the 0.50 gram sample on a gram per gram basis relative to the total capacity of the 0.10 gram sample on a gram per gram basis. The gel blocking ratio was calculated at t(minutes)=1, 5, 10 and 60. A table is provided below summarizing the absorbency characteristics and the gel blocking ratio of the commercially available superabsorbent Sumitomo BA-40B.

| Time (min) | Absorbency (g/g) for 0.1 g SAP | Absorbency (g/g) for 0.5 g SAP | Gel Blocking Ratio |
| --- | --- | --- | --- |
| 1 | 34.9 | 10.4 | 0.30 |
| 5 | 37.6 | 27.0 | 0.72 |
| 10 | 37.9 | 29.2 | 0.77 |
| 60 | 38.8 | 29.8 | 0.77 |

As shown above, superabsorbents useful in the present invention preferably have a gel blocking ratio at 1 minute of at least about 0.25. As shown above, superabsorbents useful in the present invention have a gel blocking ratio at five minutes of at least about 0.50, more preferably at least about 0.60 and most preferably at least about 0.72.

Main Body-Barrier Layer

Underlying the absorbent layer 44 is a barrier layer 50 comprising liquid-impervious film material so as to prevent liquid that is entrapped in the absorbent system 44 from egressing the sanitary napkin and staining the wearer's undergarment. The barrier layer 50 is preferably made of polymeric film, although it may be made of liquid impervious, air-permeable material such as repellent-treated non-woven or micropore films or foams.

Positioning adhesive 58 may be applied to a garment facing side of the barrier layer for securing the napkin 20 to the garment during use. The positioning adhesive 58 may be covered with removable release paper 60 so that the positioning adhesive is covered by the removable release paper 60 prior to use.

The barrier layer may be breathable, i.e., permits vapor to transpire. Known materials for this purpose include non-woven materials and microporous films in which microporosity is created by, inter alia, stretching an oriented film. Single or multiple layers of permeable films, fabrics, melt-blown materials, and combinations thereof that provide a tortuous path, and/or whose surface characteristics provide a liquid surface repellent to the penetration of liquids may also be used to provide a breathable backsheet. The cover layer 42 and the barrier layer 50 are joined along their marginal portions so as to form an enclosure or flange seal that maintains the absorbent layer 44 captive. The joint may be made by means of adhesives, heat-bonding, ultrasonic bonding, radio frequency sealing, mechanical crimping, and the like and combinations thereof.

Absorbent articles of this invention may or may not include wings, flaps or tabs for securing the absorbent article to an undergarment. Wings, also called, among other things, flaps or tabs, and their use in sanitary protection articles is described in U.S. Pat. No. 4,687,478 to Van Tilburg; U.S. Pat. No. 4,589,876 also to Van Tilburg, U.S. Pat. No. 4,900,320 to McCoy, and U.S. Pat. No. 4,608,047 to Mattingly. The disclosures of these patents are incorporated herein by reference in their entirety. As disclosed in the above documents, wings are generally speaking flexible and configured to be folded over the edges of the underwear so that the wings are disposed between the edges of the underwear.

The absorbent article of the present invention may be applied to the crotch by placing the garment-facing surface against the inside surface of the crotch of the garment. Various methods of attaching absorbent articles may be used. For example, chemical means, e.g., adhesive, and mechanical attachment means, e.g., clips, laces, ties, and interlocking devices, e.g., snaps, buttons, VELCRO (Velcro USA, Inc., Manchester, N.H.), zipper, and the like are examples of the various options available to the artisan.

Adhesive may include pressure sensitive adhesive that is applied as strips, swirls, or waves, and the like. As used herein, the term pressure-sensitive adhesive refers to any releasable adhesive or releasable tenacious means. Suitable adhesive compositions, include, for example, water-based pressure-sensitive adhesives such as acrylate adhesives. Alternatively, the adhesive composition may include adhesives based on the following: emulsion or solvent-borne adhesives of natural or synthetic polyisoprene, styrene-butadiene, or polyacrylate, vinyl acetate copolymer or combinations thereof; hot melt adhesives based on suitable block copoylmers—suitable block copolymers for use in the invention include linear or radial co-polymer structures having the formula (A–B)x wherein block A is a polyvinylarene block, block B is a poly(monoalkenyl) block, x denotes the number of polymeric arms, and wherein x is an integer greater than or equal to one. Suitable block A polyvinylarenes include, but are not limited to Polystyrene, Polyalpha-methylstyrene, Polyvinyltoluene, and combinations thereof. Suitable Block B poly(monoalkenyl) blocks include, but are not limited to conjugated diene elastomers such as for example polybutadiene or polyisoprene or hydrogenated elastomers such as ethylene butylene or ethylene propylene or polyisobutylene, or combinations thereof. Commercial examples of these types of block copolymers include Kraton™ elastomers from Shell Chemical Company, Vector™ elastomers from Dexco, Solprene™ from Enichem Elastomers and Stereon™ from Firestone Tire & Rubber Co.; hot melt adhesive based on olefin polymers and copolymers where in the olefin polymer is a terpolymer of ethylene and a co-monomers, such as vinyl acetate, acrylic acid, methacrylic acid, ethyl acrylate, methyl acrylate, n-butyl acrylate vinyl silane or maleic anhydride. Commercial examples of these types of polymers include Ateva (polymers from AT plastics), Nucrel (polymers from DuPont), Escor (from Exxon Chemical).

Where adhesive is used, a release strip may be applied to protect the adhesive on the absorbent article prior to attaching the absorbent article to the crotch. The release strip can be formed from any suitable sheet-like material adheres with sufficient tenacity to the adhesive to remain in place prior to use but which can be readily removed when the absorbent article is to be used. Optionally, a coating may be applied to release strip to improve the ease of removability of the release strip from the adhesive. Any coating capable of achieving this result may be used, e.g., silicone.

Any or all of the cover, absorbent layer, transfer layer, backsheet layer, and adhesive layers may be colored. Such coloring includes, but is not limited to, white, black, red, yellow, blue, orange, green, violet, and mixtures thereof. Color may be imparted according to the present invention through dying, pigmentation, and printing. Colorants used according the present invention include dyes and inorganic and organic pigments. The dyes include, but are not limited to, anthraquinone dyes (Solvent Red 111, Disperse Violet 1, Solvent Blue 56, and Solvent Green 3), Xanthene dyes (Solvent Green 4, Acid Red 52, Basic Red 1, and Solvent Orange 63), azine dyes (Jet black), and the like. Inorganic pigments include, but are not limited to, titanium dioxide (white), carbon black (black), iron oxides (red, yellow, and brown), chromium oxide (green), ferric ammonium ferrocyanide (blue), and the like.

Organic pigments include, but are not limited to diarylide yellow AAOA (Pigment Yellow 12), diarylide yellow AAOT (Pigment Yellow 14), phthalocyanine blue (Pigment Blue 15), lithol red (Pigment Red 49:1), Red Lake C (Pigment Red), and the like.

The absorbent article may include other known materials, layers, and additives, such as, foam, net-like material, perfumes, medicaments or pharmaceutical agents, moisturizers, odor control agents, and the like. The absorbent article can optionally be embossed with decorative designs.

The absorbent article may be packaged as unwrapped absorbent articles within a carton, box or bag. The consumer withdraws the ready-to-use article as needed. The absorbent article may also be individually packaged (each absorbent article encased within an overwrap).

Also contemplated herein include asymmetrical and symmetrical absorbent articles having parallel longitudinal edges, dog bone- or peanut-shaped, as well as articles having a tapered construction for use with thong-style undergarments.

From the foregoing description, one skilled in the art can ascertain the essential characteristics of this invention, and without departing from the spirit and scope thereof, can make various changes and modifications. Embodiments set forth by way of illustration are not intended as limitations on the variations possible in practicing the present invention.

Inventive Sample

Inventive Sample #1 A sanitary napkin having a barrier layer of 0.9 mil polyethylene film produced by Pliant Corp, Schaumberg, Ill., product code #3492A with 5.9 mg/sq in of Fuller 1023 adhesive applied to the cover facing surface of the barrier, a 75 gsm spunlace cover material commercially available from Polymer Group, Inc., Charlotte, N.C., as product code PGI 4012, and 2.6 mg/sq in of Fuller 1023 adhesive, commercially available from Fuller Corp., St. Paul, Minn., on the barrier facing side of the cover. Between the cover and barrier is a layer of Little Rapids type 2004 wetlaid tissue paper, commercially available from Little Rapids, Corp., Green Bay, Wis., with a basis weight of 21.2 gsm. The edges of the tissue layer were about 10 mm inboard of the edges of the cover and barrier. The barrier facing side of the tissue had a area of approximately 50 mm wide by 170 mm long coated with 10 gsm of Fuller 1023 adhesive. Prior to the tissue and adhesive being joined to the barrier and cover a 130 gsm layer of Sumitomo BA40B superabsorbent, commercially available from Sumitomo Seika Chemicals, Co., Ltd., Osaka, Japan, was deposited onto the adhesive covered side of the tissue. The adhesive held the superabsorbent in place. After deposition of the superabsorbent, the cover, SAP covered tissue and barrier layers were joined. The garment facing surface of the barrier was coated with 20 mg/sq inch of a pressure sensitive adhesive intended for panty attachment, Fuller 1417, commercially available from Fuller Corp., St. Paul, Minn.

Applications of the absorbent article according to the present invention for sanitary and other health-care uses can be accomplished by any sanitary protection, incontinence, medical and absorbent methods and techniques as are presently or prospectively known to those skilled in the art. Thus, it is intended that the present application cover the modifications and variations of this invention provided that they come within the scope of the appended claims and their equivalents.

We claim:

1. An absorbent article comprising:
   a cover layer;
   a barrier layer; and
   an absorbent system arranged between said cover layer and said barrier layer, said absorbent system comprising superabsorbent polymer (SAP);
   wherein said absorbent article has a drape angle at x=50 of less than 80° and a drape angle at x=100 of less than 50° and said absorbent article has an absorbency index (AI) of greater than about 1.5.

2. The absorbent article according to claim 1, wherein said absorbent article has a drape angle at x=50 of less than 70° and a drape angle at x=100 of less than 40°.

3. The absorbent article according to claim 1, wherein said absorbent article has a drape angle at x=50 of less than 60° and a drape angle at x=100 of less than 30°.

4. The absorbent article according to claim 1, wherein said absorbent article has a drape angle at x=150 of less than 25°.

5. The absorbent article according to claim 1, wherein said absorbent article has a drape angle at x=150 of less than 15°.

6. The absorbent article according to claim 1, wherein said superabsorbent has a gel blocking ratio at one minute of at least about 0.30.

7. The absorbent article according to claim 1, wherein said SAP has a gel blocking ratio at five minutes of at least about 0.72.

8. The absorbent article according to claim 1, wherein said SAP has a gel blocking ratio at five minutes of at least about 0.77.

9. The absorbent article according to claim 1, wherein said absorbent article has an absorbency index (AI) of greater than about 1.7.

10. The absorbent article according to claim 1, wherein said absorbent article has an absorbency index (AI) of greater than about 1.8.

11. The absorbent article according to claim 1, wherein said absorbent article has a thickness less than about 2.5 mm.

12. The absorbent article according to claim 1, wherein said absorbent article has a thickness of less than about 2.0 mm.

13. The absorbent article according to claim 1, wherein said absorbent article has a thickness of less than about 1.5 mm.

14. The absorbent article according to claim 1, wherein said SAP is present in an amount of at least 50 gsm.

15. The absorbent article according to claim 3, wherein said SAP is present in an amount of between about 100 gsm and about 150 gsm.

16. The absorbent article according to claim 1, wherein said SAP is secured to a cover facing side of said barrier layer.

17. The absorbent article according to claim 1, wherein said absorbent system comprises a layer arranged between said cover and said barrier, said SAP secured to a surface of said layer arranged between said cover and said barrier.

18. The absorbent article according to claim 1, wherein said absorbent systems consists of SAP is secured to an internal surface of said cover or said barrier.

19. The absorbent article according to claim 1, wherein said cover layer is a spunlace material including from about 10 to about 65 wt % rayon and from about 35 to about 90 wt % polyester.

20. An absorbent article comprising:
    a cover layer;
    a barrier layer; and
    an absorbent system arranged between said cover layer and said barrier layer, said absorbent system comprising superabsorbent polymer (SAP);
    wherein said absorbent article has a drape angle at x=50 of less than 80° and a drape angle at x=100 of less than 50° and said absorbent article has an absorbency index (AI) of greater than about 1.5; and
    wherein said absorbent article has a thickness less than about 2.5 mm.

* * * * *